US00PP14823P2

(12) United States Plant Patent

Snoeijer

(10) Patent No.: US PP14,823 P2
(45) Date of Patent: May 25, 2004

(54) CLEMATIS PLANT NAMED 'PRETTY IN BLUE'

(50) Latin Name: *Clematis×hybrida*
Varietal Denomination: Pretty in Blue

(75) Inventor: Wim Snoeijer, Gouda (NL)

(73) Assignee: Plant Haven, Inc., Santa Barbara, CA (US)

( * ) Notice: Subject to any disclaimer, the term of this patent is extended or adjusted under 35 U.S.C. 154(b) by 75 days.

(21) Appl. No.: 10/366,018

(22) Filed: Feb. 13, 2003

(51) Int. Cl.[7] ..... A01H 5/00
(52) U.S. Cl. ..... Plt./228
(58) Field of Search ..... Plt./228

(56) References Cited

PUBLICATIONS

GTITM UPOVROM Citation for 'Pretty in Blue' as per QZ PBR 010074; Jan. 15, 2001.*

* cited by examiner

*Primary Examiner*—Kent Bell
(74) *Attorney, Agent, or Firm*—Planthaven, Inc.; Geoffrey Needham

(57) ABSTRACT

A new cultivar of Clematis named 'Pretty in Blue' that is characterized by upright violet-blue flowers in spring, summer and autumn, upright to decumbent habit, long blooming period, and medium-green foliage In combination, these traits set 'Pretty in Blue' apart from all other existing varieties of Clematis known to the inventor.

2 Drawing Sheets

Genus: Clematis.
Species: ×*hybrida*.
Denomination: Pretty in Blue.

BACKGROUND OF THE INVENTION

The present invention relates to a new and distinct cultivar of Clematis that is grown for use as an ornamental in the landscape. The new cultivar is known botanically as Clematis and will be referred to hereinafter by the cultivar name 'Pretty in Blue'.

'Pretty in Blue' resulted from a formal breeding program that was established by the inventor in 1992 in Boskoop, Holland. The purpose of the breeding program was to find out if the inventor could successfully crossbreed two species, which had not been accomplished in 140 years, and in doing so produce hardy varieties that are easy to propagate, exhibit improved flower color and resistance to pests and disease.

The female parent plant is *Clematis integrifolia* 'Olgae' (unpatented) and the male parent plant is *Clematis recta* (unpatented). 'Pretty in Blue' is a hybrid plant that resulted from the hybridization between the pollen parent *Clematis recta* and the seed parent *Clematis integrifolia* 'Olgae'. The cross was conducted by the inventor in a cultivated area of Boskoop, Holland and 'Pretty in Blue' was selected by the inventor in 1996 based on the unique flowers, long blooming period, ease of propagation, and free-flowering.

'Pretty in Blue' is a perennial exhibiting an upright to decumbent habit, upright violet-blue flowers with contrasting yellow stamens, large inflorescences and a long period of free-flowering. Propagation is accomplished using softwood cuttings. The closest comparison plant is Clematis 'Aromatica' (unpatented). 'Pretty in Blue' is distinguishable from 'Aromatica' by a longer blooming period and ability to be easily and readily propagated. 'Pretty in Blue' differs from the female parent plant in flower color and habit, while differing from the male parent plant in flower color.

The first asexual propagation was accomplished by the inventor in 1996 in a cultivated area of Boskoop, Holland. Asexual propagation of the new cultivar by cuttings at the location previously stated, has shown that the unique features of the new Clematis cultivar 'Pretty in Blue' are stable and the plant reproduces true to type in successive generations of asexual propagation.

SUMMARY OF THE INVENTION

The following represent the distinguishing characteristics of the new Clematis cultivar 'Pretty in Blue'. In combination these traits set 'Pretty in Blue' apart from all other existing varieties of Clematis known to the inventor. 'Pretty in Blue' has not been tested under all possible conditions and phenotypic differences may be observed with variations in environmental, climatic, and cultural conditions, however, without any variance in genotype.

1. Clematis 'Pretty in Blue' exhibits upright violet-blue flowers with contrasting yellow stamens.
2. Clematis 'Pretty in Blue' is free-flowering and blooms over a long period of time.
3. Clematis 'Pretty in Blue' is readily propagated using softwood cuttings.
4. Clematis 'Pretty in Blue' exhibits an upright to decumbent habit.
5. Clematis 'Pretty in Blue' exhibits medium-green foliage.
6. Clematis 'Pretty in Blue' is a perennial exhibiting large inflorescences.
7. Clematis 'Pretty in Blue' is hardy to USDA Zones 5&6.

BRIEF DESCRIPTION OF THE DRAWINGS

The accompanying color drawings illustrate the overall appearance of the new Clematis variety 'Pretty in Blue' showing the colors as true as it is reasonably possible to obtain in colored reproductions of this type. Colors in the drawings may differ from the color values cited in the detailed botanical description, which accurately describe the actual colors of the new variety 'Pretty in Blue'.

The drawing on sheet 1 illustrates the foliage, stem and blooms from a side perspective.

The drawing on sheet 2 is a close-up view of the flowers. All drawings are made using conventional techniques and although foliage colors may appear different from actual colors due to light reflectance, they are as accurate as possible by conventional photography.

BOTANICAL DESCRIPTION OF THE PLANT

The following is a detailed description of the Clematis cultivar named 'Pretty in Blue'. Data was collected from 2-year-old plants in 2-litre containers grown out-of-doors in Boskoop, Holland. Color determinations are in accordance with The 2001 Royal Horticultural Society Colour Chart except where general color terms of ordinary dictionary significance are used. The growing requirements are similar to the species.

Botanical classification: Clematis 'Pretty in Blue'.
Species: ×*hybrida*.
Common name: Vase vine.
Use: Ornamental.
Parentage: 'Pretty in Blue' is a hybrid resulting from the hybridization of the following parent plants:
- *Seed parent.*—*Clematis integrifolia* 'Olgae'.
- *Pollen parent.*—*Clematis recta*.

Type: Perennial.
Vigor: Low vigor.
Sexuality: Bisexual.
Habit: Upright to decumbent.
Height (at maturity): 150 cm. in height.
Width (at maturity): 75 cm. in width.
Hardiness: USDA Zones 5&6.
Propagation: Softwood cuttings.
Root system: Fine and fleshy.
Soil: All moist but well-drained soils.
Sunlight: Full sun and partial shade.
Time to initiate rooting: 4 weeks are needed to produce roots on an initial cutting.
Temperature to initiate rooting: 20° to 30° Centigrade air temperature.
Crop time: 12 months are needed to produce a finished 1-litre container from a rooted cutting.
Seasonal interest: Violet-blue flowers in spring, summer and autumn.
Disease and pests: Susceptible to mildew.
Stem:
- *Stem diameter.*—0.5 cm. in diameter.
- *Stem length.*—1.5 meters in length.
- *Surface.*—Glabrous.
- *Lenticels.*—None present.
- *Stem color.*—A combination of 141C and 77A.
- *Internode length.*—8–18 cm. between nodes.
- *Branching habit.*—Basal shoots.

Foliage:
- *Type.*—Deciduous.
- *Leaf arrangement.*—Opposite.
- *Leaf division.*—Compound pinnate.
- *Number of leaflets.*—Two to five leaflets in number.
- *Leaflet shape.*—Lanceolate.
- *Leaflet base.*—Oblique.
- *Leaflet apex.*—Acute.
- *Leaflet venation.*—Palmate.
- *Leaflet attachment.*—When more than two leaflets the basal pair and the terminal leaflet may be attached with a petiolule. Otherwise the leaflets are sessile.
- *Petiolule length.*—0 cm. to 1.2 cm. in length.
- *Petiolule diameter.*—0.15 cm. in diameter.
- *Petiolule color.*—143C.
- *Petiolule surface.*—Sparsely hairy.
- *Leaflet dimensions.*—4–10 cm. in length and 1–4 cm. in width.
- *Vein color* (*adaxial surface*).—147D.
- *Vein color* (*abaxial surface*).—147D.
- *Leaf surface* (*adaxial*).—Glabrous.
- *Leaf surface* (*abaxial*)—Mostly glabrous with sparsely hairy veins.
- *Leaf pubescence.*—Absent.
- *Leaf texture.*—Leathery.
- *Leaf attachment.*—Leaf is attached by a rachis.
- *Leaf dimensions.*—13 cm. in length and 12 cm. in width.
- *Rachis dimensions.*—5 cm. in length and 3–4 mm. in width.
- *Rachis color.*—143C.
- *Rachis surface.*—Sparsely hairy.
- *Stipules.*—Absent.
- *Leaf margin.*—Entire and lobed.
- *Leaflet color* (*adaxial surface*).—147A.
- *Leaflet color* (*abaxial surface*).—147C.
- *Foliar fragrance.*—Grass-like.

Flower:
- *Blooming season.*—Late spring to early autumn.
- *Inflorescence type.*—Dichasial cyme.
- *Flower arrangement.*—Spiral.
- *Color of peduncle.*—A combination of 141C and 77A.
- *Peduncle length.*—5–9 cm. in length.
- *Peduncle width.*—0.1 cm. in width.
- *Peduncle surface.*—Puberulent.
- *Self-cleaning or persistent.*—Self-cleaning.
- *Dimensions of flower.*—2 cm. in height and 6 cm. in diameter.
- *Flower shape.*—Rotate.
- *Aspect.*—Upright.
- *Petals.*—Apetalous.
- *Tepals.*—Four tepals.
- *Color of tepals* (*adaxial and abaxial surfaces*).—86A.
- *Tepal shape.*—Elliptic.
- *Tepal base.*—Broadly cuneate.
- *Tepal apex.*—Obtuse.
- *Tepal surface* (*adaxial surface*).—Glabrous.
- *Tepal surface* (*abaxial surface*).—Glabrous.
- *Tepal margin.*—Entire.
- *Tepal length.*—2.5 cm. in length.
- *Tepal width.*—0.9 cm. in width.
- *Unfused or fused.*—Tepals are unfused.
- *Bud color.*—93A.
- *Bud shape.*—Elliptic.
- *Bud dimensions.*—1.5 cm. in length and 0.6 cm. in width.
- *Quantity of flowers per branch.*—Approximately 200 per branch.
- *Lastingness of flower.*—An individual flower will last 15 days on a plant (from the opening of the bud to the tepals falling off), and 8–10 days off the plant.
- *Fragrance.*—Sweet.

Reproduction organs:
- *Stamens.*—+50.

*Color of stamens.*—10D.
*Dimensions of stamen.*—0.4–0.8 cm. in length and 0.1 cm. in width.
*Dimensions of anther.*—10 mm. in width and 25 mm. in length.
*Pollen color.*—10D.
*Amount of pollen.*—Small amount.
*Anther color.*—10D.
*Anther shape.*—Filiform.
*Pistils.*—+30.
*Pistil shape.*—Plumose.
*Pistil color.*—155A.
*Stigma color.*—155A.
*Ovary position.*—Superior.
*Ovary color.*—Green.

Seed: No seed has been observed to date.

I claim:

1. A new and distinct variety of Clematis plant named 'Pretty in Blue' as described and illustrated.

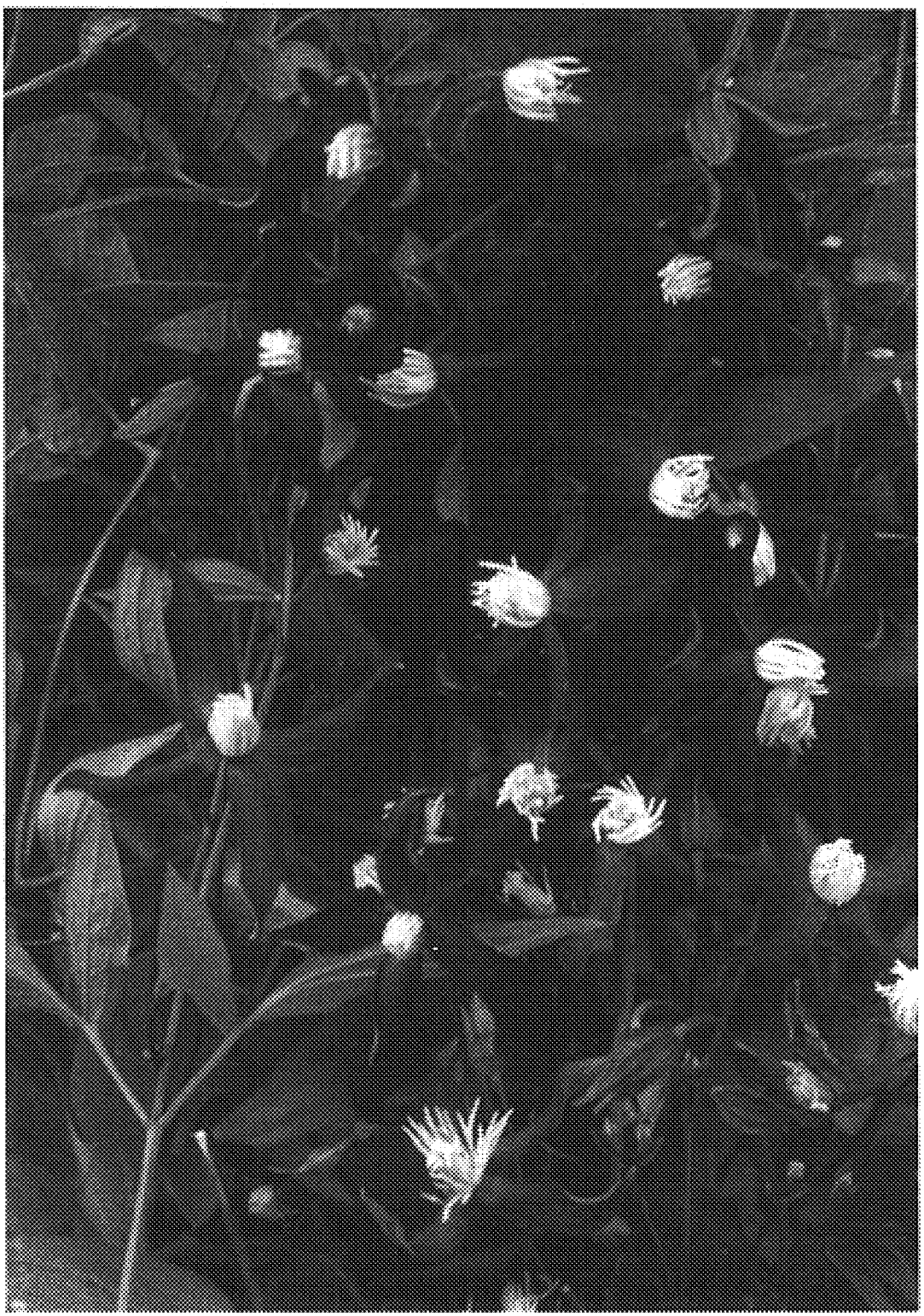

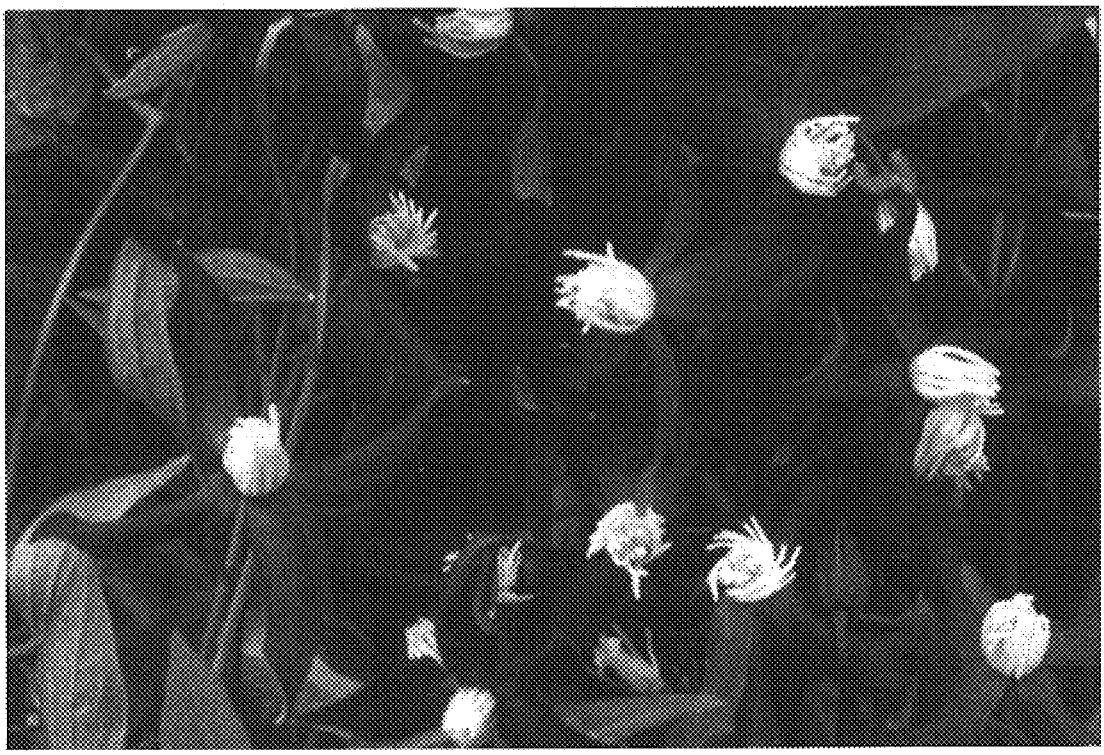

* * * * *